United States Patent [19]

Rehwald

[11] Patent Number: 4,741,212
[45] Date of Patent: May 3, 1988

[54] METHOD FOR DETERMINING STRUCTURAL DEFECTS IN SEMICONDUCTOR WAFERS BY ULTRASONIC MICROSCOPY

[75] Inventor: Walther Rehwald, Wettingen, Switzerland

[73] Assignee: General Electric Company, Schenectady, N.Y.

[21] Appl. No.: 891,170

[22] Filed: Jul. 31, 1986

[51] Int. Cl.⁴ ............................................. G01N 29/04
[52] U.S. Cl. ........................................ 73/600; 73/618
[58] Field of Search .................. 73/600, 599, 618, 642

[56] References Cited

U.S. PATENT DOCUMENTS

| | | | |
|---|---|---|---|
| 2,971,372 | 2/1961 | Lewis et al. | 73/600 |
| 4,008,602 | 2/1977 | Love . | |
| 4,011,748 | 3/1977 | Bond et al. . | |
| 4,028,933 | 6/1977 | Lemons et al. . | |
| 4,366,713 | 1/1983 | Gilmore et al. | 73/618 |

OTHER PUBLICATIONS

M. Moghisi et al., "An Inexpensive Computer-Controlled Ultrasonic C-Scan System," *NDT International*, vol. 16, No. 1, Feb. 1983, pp. 9-12.

*Primary Examiner*—John Chapman
*Attorney, Agent, or Firm*—Donald S. Cohen; James M. Trygg; Allen LeRoy Limberg

[57] ABSTRACT

A method and apparatus for determining the location and size of structural defects in a body of solid material, particularly regions of thermoplastic deformation in semiconductor wafers. An acoustical focused beam generated by an ultrasonic transducer, having a pulsed frequency of at least 75 MHZ, is transmitted through the body to provide an attenuated signal pattern which manifests structural defects, such as slip planes which can result in wafer warp, as well as cracks, bubbles, foreign particles or segregation zones and internal interfaces.

5 Claims, 3 Drawing Sheets

METHOD FOR DETERMINING STRUCTURAL DEFECTS IN SEMICONDUCTOR WAFERS BY ULTRASONIC MICROSCOPY

This invention relates to a method and apparatus for locating and quantifying structural damage in semiconductor wafers utilizing ultrasonic microscopy.

BACKGROUND OF THE INVENTION

In the processing of semiconductor substrates, such as silicon wafers, to make devices, many steps of heating and cooling the wafer are used. During these processing steps, the heating and cooling operations produce a non-uniform temperature distribution in the wafer which results in thermoelastic stresses. When such thermoelastic stresses are forced to go beyond the strongly temperature-dependent yield stress, a phenomenon known as plastic flow occurs along the slip planes of the crystalline structure of the wafer. The stress causing this plastic flow results not only in a high dislocation density of the structure of the wafer, but also a permanent strain in the form of an elongation within regions close to the rim or peripheral portions of the wafer causing warpage of the wafer. These problems become more severe as the size of the wafer increases.

Heretofore, the techniques for detecting warping depended upon the use of geometric measurements, such as profilometers. Moreover, in order to determine the location of slip planes, etching techniques are needed to render them visible at the surface. However, this is a destructive test. Other techniques, such as x-ray topography and special electron microscopy techniques for observing dislocations are too sophisticated and take too much time for wafer testing as a routine process. Therefore, it is desirable to have a technique for determining the location and extent of slip planes, which technique is relatively easy to carry out and which is non-destructive of the wafer.

SUMMARY OF THE INVENTION

Structural defects in a body of solid material in the form of plane parallel plates are located and quantified by focusing an incident beam of acoustic energy within the body, with the incident beam having a wavelength that is significantly smaller than the thickness of the body and a beam waist diameter that is smaller than the thickness of the body. Relative movement is provided between the body and the beam so that a portion of the surface of the body is scanned in a given direction. A positive signal indicative of the position of the surface portion receiving the beam is provided and the acoustic energy of the beam transmitted through the body is detected and an electrical signal corresponding to the attenuation of the acoustic beam through the body is produced. The produced electrical signal is processed such that attenuation peaks in the signal are indicative of the location and magnitude of a structural defect in the body.

DETAILED DESCRIPTION OF THE PREFERRED EMBODIMENT OF THE INVENTION

The present invention provides the means and technique for locating and quantifying structural defects in a body of solid material. Semiconductor wafers, for example, made of silicon, when subjected to the various heating and cooling steps in the processing of the wafer, produce thermal stresses that can lead to plastic flow. For example, the material investigated in this embodiment is a flat wafer of single-crystal silicon. The thermal stresses can cause a plastic deformation that is manifested as slip planes running from the periphery into the interior and being inclined about 35 degrees against the wafer normal. Since the outer regions of the wafer are permanently stretched or possibly elongated, thermoplastic deformation leads to warping of the entire wafer.

Figure 1:
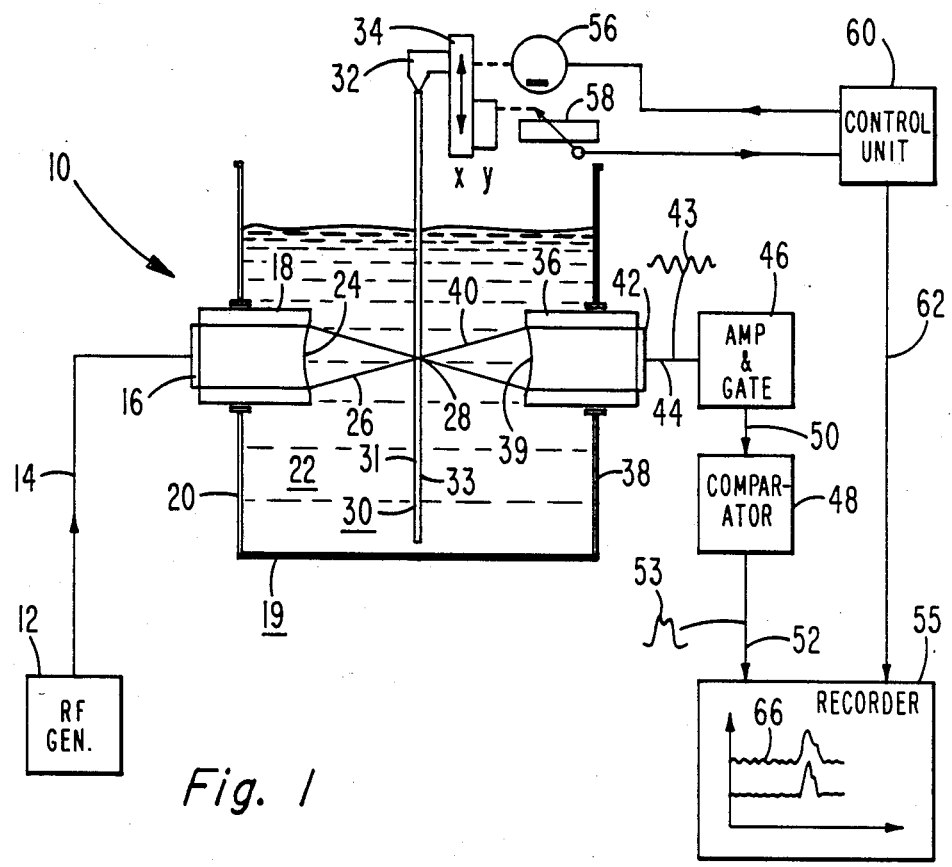
FIG. 1 is a schematic of a form of an apparatus for carrying out the acoustic energy beam method for determining structural defects in a body, such as a wafer, according to the present invention.

The apparatus shown in FIG. 1 provides a means to determine not only the location of slip plane damage that may exist in a wafer but also provides an indication of the size and density of the slip plane defect by an attenuation signal representing the acoustical energy losses in transmission through the wafer, as will be described. The invention provides a means not only for determining slip planes, but also cracks, air bubbles, foreign particles, segregation zones and internal interfaces.

The apparatus 10 comprises a conventional pulsed radio frequency (RF) generator 12 providing short pulses of RF energy, for example, pulses of 1 $\mu$s duration of 90 MHz frequency, sent over a path 14 to an ultrasonic transducer 16 integrally bonded to an acoustic lens 18 mounted in one wall 20 of a container 19 for holding a liquid bath 22, such as water. The transducer 16 is formed of X-quartz. The lens 18 is formed of fused quartz or any other low-attenuation material and is provided with a concave surface 24 shaped to focus the acoustic beam 26 to a desired focal point 28.

A silicon wafer 30 is properly supported by three pins within a frame 32 which in turn is moved by an X-Y stage 34 in a vertical (X) and horizontal (Y) direction to effect a scan across the surface of the wafer. A second lens 36 is mounted in a second wall 38 of the container 19. The lens 36 is provided with a concave surface 39 mirror symmetrical with the shape of the surface 24 of the lens 18. The lens 36 is focused to a focal point 28 to receive a transmitted acoustic signal 40 after passing through the wafer 30.

The incident acoustic beam 26 and the acoustic beam 40 transmitted through the wafer 31 have a waist diameter (2w) of 0.2 millimeter (mm) at an RF signal (15) frequency (f) of 90 MHz, which, due to a non-perfect spherical lens shape, is larger than the value determined by diffraction. Since the slip planes are inclined and cover a projected width of 0.23 mm in a 0.4 mm thick wafer, the obtained lateral resolution is sufficient for their localization.

An ultrasonic transducer 42, similar to the transducer 16, is bonded to the lens 36 to detect the transmitted acoustic beam 40 after collection through the lens 36. The detected signal 43 is applied on an electrical path 44 to conventional processing circuits 46 for amplification and gating of the detected signal and a logarithmic converter 48 that compares the transmitted signal with a reference signal, fed in from the RF-generator 12 via a variable attenuator, and outputs an attenuation signal 53, calibrated in decibels (dB). The circuits 46 and 48 are suitably a MATEC attenuation recorder, model 2074A, available from MATEC, Inc., Warwick, R.I. or any other circuitry delivering a signal as a measure for the attenuation in the electric circuit between the input 14 and the output 44. The attenuation signal is added to a negative DC signal representing the y-position of the scan and applied to the y-input of an X-Y recorder 55.

The stage 34 is mechanically driven by screw spindles connected to stepper motors 56. A control unit 60 activates the stepper motors 56 in a programmed fashion, where the length of the x- and y-scans, as well as the number of scans, can be preselected. This unit also activates the pen of the x-y-recorder. The movable parts of the x-y stage 34 are mechanically connected to two linear potentiometers that give a voltage proportional to the linear shift to either the x-input of the recorder or, combined with the attenuation signal to the y-input.

Both signals may also be applied to a computer for storage of data corresponding to those attenuation and position signals for later use rather than for an immediate display.

Figure 2:
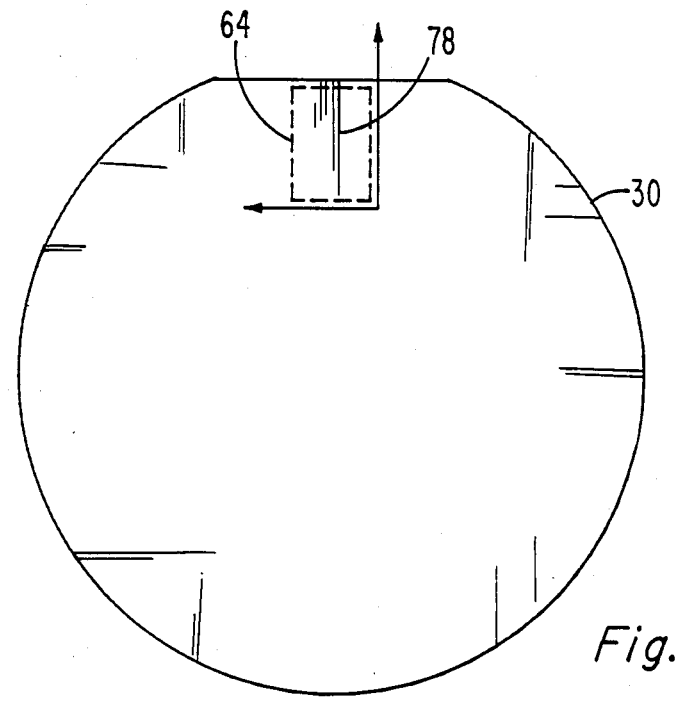
FIG. 2 is a plan view of a wafer showing the portions that are scanned, e.g., in the X and Y direction.

In operation, a wafer 30 is positioned in the focus of the apparatus 10 as shown. The wafer 30 is scanned relative to the focal point 28 to cover an area 64 of the surface 31 as shown in FIG. 2. The signals 15 from the RF generator 12 cause the transducer 16 to provide a pulsed acoustic vibration of 90 MHz which is coupled through the lens 18 to provide a beam 26 focused in the central plane of the wafer 30 as shown in detail in FIG. 4.

The incident acoustic signal 26 is transmitted through the wafer 30. Beyond the focal point 28, the acoustic beam 40 (termed herein, the transmitted acoustic beam 40) expands and fills the surface 39 of the lens 36. The lens 36 couples the acoustic vibrations of beam 40 to the transducer 42, which in turn, provides the electrical signal 43 on path 44 to the processing circuit 46. A signal 53 representing the attenuation of the incident acoustic beam 26 is applied to the recorder 55, which in turn, provides a scan in the form of an attenuation signal 66 (See FIG. 3) as the wafer 30 is moved in an X direction through the focal point 28.

Figure 5:
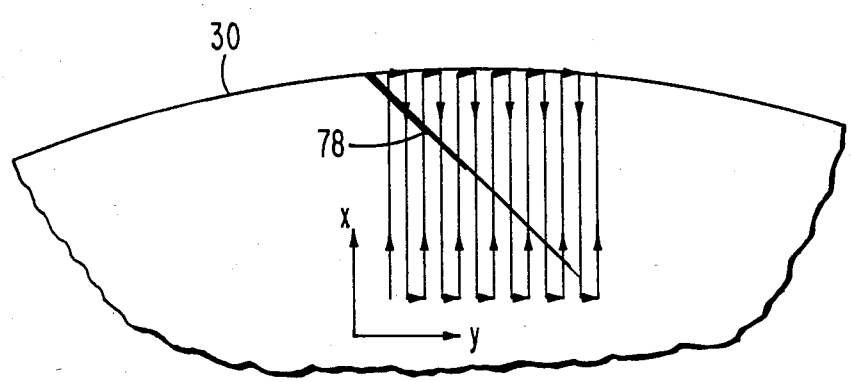
FIG. 5 is an enlarged view of a portion of a wafer and the scanning motion.

As shown in FIG. 5, at the end of each scan, the wafer 30 is shifted in the y-position by, for example, 0.5 mm to a new starting position and then scanned along the X direction with alternating senses of movement within the area 64 in FIG. 2. From the recorded scan lines shown in FIG. 3, it will be noticed that a series of attenuation peaks 70, 72, 74 and 76 appear in the respective waveform patterns 71, 73, 75 and 77, etc. These peaks correspond to the exact location of a slip plane 78, as shown in FIG. 5, caused by a thermoplastic deformation due to the heating and cooling of the wafer 30, as explained above. The slip plane 78 had been determined also by etching the surface 31 of the wafer 30 as a control, but there is no difference in the acoustic signal before and after etching. Repeated scanning of the wafer 30 provides identical and reproducible patterns 71, 73, etc. manifesting the attenuation peaks 70, 72, etc. Moreover, the amplitude of the peaks corresponds to the dislocation density in the slip plane 78 and thus provides a means to quantify the damage to the wafer.

Figure 3:
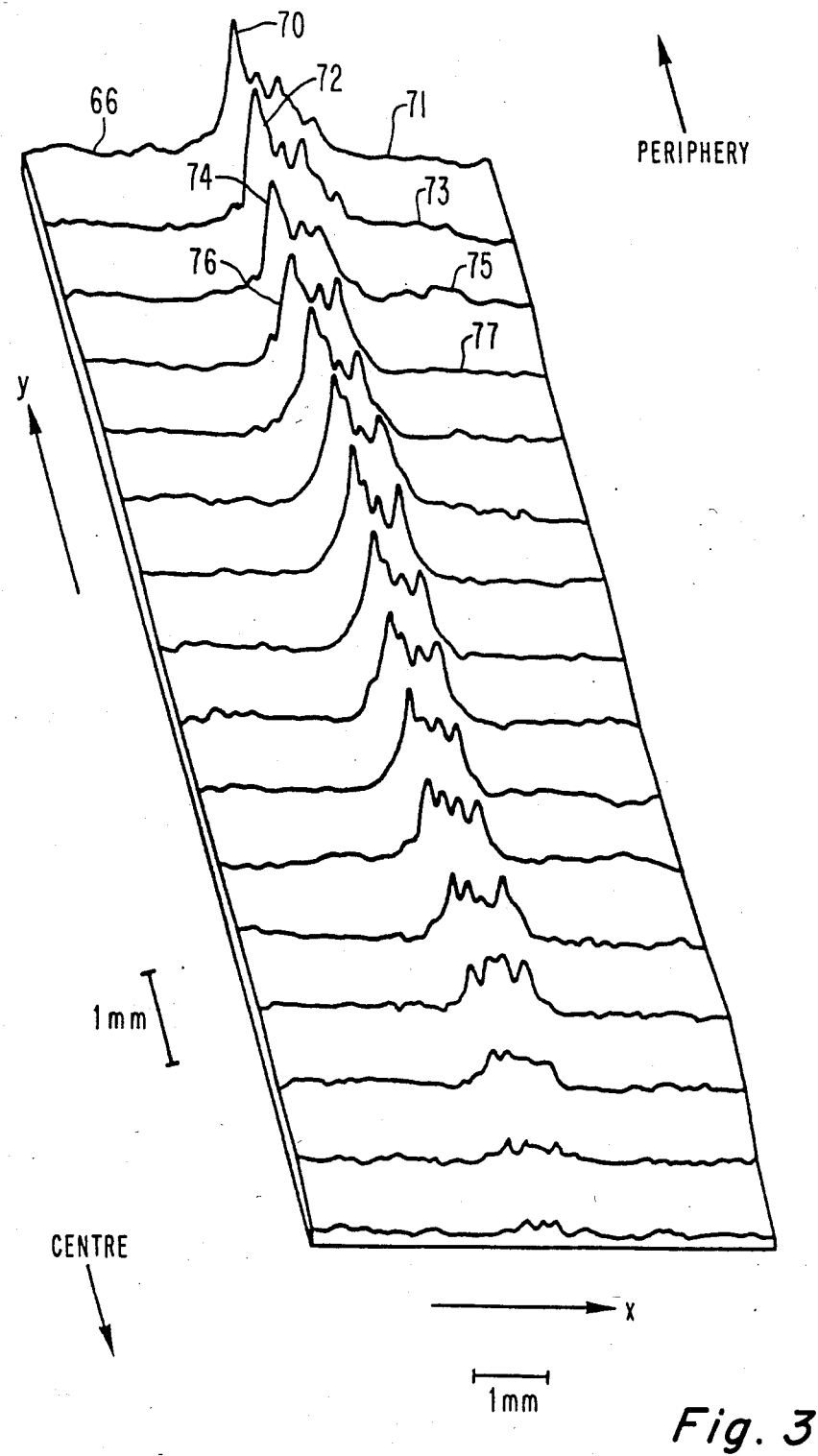
FIG. 3 shows several parallel scans across a part of the silicon wafer shown in FIG. 2 generated by the apparatus shown in FIG. 1.

In the operation of the apparatus 10 according to the invention, there is a relationship between the acoustic frequency of the incident beam 26 and the attenuation contrast as manifested by the curve plots 71, 73, etc. of FIG. 3. It is to be understood that the acoustic frequency should be at least 75 MHz and preferably on the order of 90 MHz in order to provide a measurable attenuation contrast between background and slip plane. A difference of 0.5 $\mu$B in attenuation at least is required. Moreover, it should be understood that the focusing of the beam 26 allows for a determination of the location of the damaged region within the bulk structure of the wafer 30.

It should be understood that the immersion liquid is greatly desired to reduce the reflection losses at the wafer surfaces 31 and 33 of the wafer 30 as well as reflections at the lens surfaces 24 and 38 of the lenses 18 and 36, respectively.

The invention detects and measures primarily dislocations in the slip planes of thermoplastically deformed regions. Slipped regions on a wafer cannot be used for fabricating digital or analogue devices and these regions can now be avoided. They also indicate when the dislocations are present, that warpage of the whole wafer is to be expected.

Figure 4:
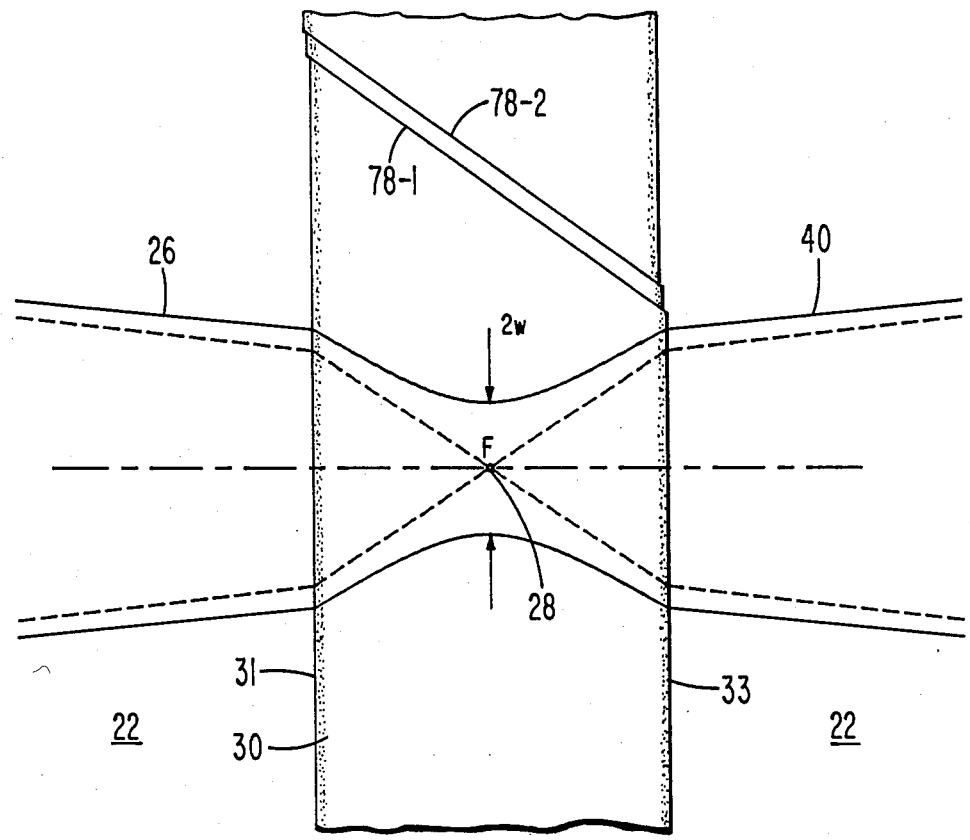
FIG. 4 is a sketch showing in detail the relationships of the waist diameter (2w), focus 28, thickness (t) of the wafer 30.

A slip plane 78 causes a shear displacement of a portion of the crystalline structure of the wafer 30 along one of the (110) directions in a (111) plane, as indicated in FIG. 4, for example. Additional slip planes, such as slip planes, 78-1 and 78-2, contribute to the elongation in tangential direction of the wafer. The elongations add up around the whole circumference of the wafer and result in a warped wafer.

While the invention has been described in terms of its use in determining thermoplastic damage in a semiconductor wafer, it should be understood that it can be used for determining defects in any solid material in the form of thin-plane-parallel plates. Any structural defect causing attenuation in the ultrasonic beam, that is, any defect that is sensitive to an acoustic (ultrasonic) beam, can be located and quantified according to the invention. As indicated above, such defects can be manifested as cracks, air bubbles, foreign particles, segregation zones and internal interfaces.

What is claimed:
1. A method for locating and quantifying a structure defect in the form of a slip plane caused by thermoplastic deformation, in a semiconductor body comprising the steps of:
(a) focusing an incident beam of acoustic energy within the body, said incident beam having a wavelength that is significantly smaller than the thickness of said body and a beam waist diameter that is smaller than the thickness of said body;
(b) providing relative movement between said body and said beam so that a portion of the major surface is scanned in a given direction;
(c) providing a position signal indicative of the position of said surface portion receiving said incident beam;
(d) detecting the acoustic energy of the beam transmitted through said body and producing a transmitted electrical signal corresponding to the attenuation of said acoustic beam through said body; and

(e) processing said transmitted electrical signal such that attenuation peaks in said transmitted signal are indicative of the location and magnitude of said structural defect in said body.

2. The method of claim 1 further comprising the step of:
(a) scanning in both X and Y directions over said surface portion to provide signal data for storage or mapping.

3. The method of claim 1 wherein said body is immersed in a liquid bath.

4. The method of claim 1 wherein said beam vibrates acoustically at a frequency that is at least 75 MHz.

5. The method of claim 1 wherein the acoustic attenuation signal is used to detect areas of excessive dislocation density and to predict warpage of a semiconductor wafer.

* * * * *